United States Patent [19]

Fietti, Jr.

[11] Patent Number: 4,782,842

[45] Date of Patent: Nov. 8, 1988

[54] ARCUATE FIXATOR

[76] Inventor: Vincent G. Fietti, Jr., 115 E. 61st St., New York, N.Y. 10021

[21] Appl. No.: 9,909

[22] Filed: Feb. 2, 1987

[51] Int. Cl.⁴ ............................................ A61M 37/00
[52] U.S. Cl. ............................ 128/92 Z; 128/92 ZW; 128/92 ZK
[58] Field of Search ............ 128/92 ZK, 92 ZW, 92 Z

[56] References Cited

U.S. PATENT DOCUMENTS

| | | | |
|---|---|---|---|
| 4,185,623 | 1/1980 | Volkov et al. | 128/92 Z |
| 4,488,542 | 12/1984 | Helland | 128/92 Z |
| 4,548,199 | 10/1985 | Agee | 128/92 ZK |
| 4,554,915 | 11/1985 | Brumfield | 128/92 Z |
| 4,604,997 | 8/1986 | De Bastiani et al. | 128/92 UD |
| 4,611,586 | 9/1986 | Agee et al. | 128/92 ZK |
| 4,628,919 | 12/1986 | Clyburn | 128/92 ZK |
| 4,628,922 | 12/1986 | Dewar | 128/92 Z |
| 4,637,382 | 1/1987 | Walker | 128/92 Z |

Primary Examiner—C. Fred Rosenbaum
Assistant Examiner—Colleen M. Reilly
Attorney, Agent, or Firm—Pasquale A. Razzano

[57] ABSTRACT

A device for use in setting of fractured wrist or other wrist disorders including a rigid rod member adjustable in length, a pair of holders fastened to the member and each carrying at least one transcutaneous pin which is intended to penetrate the skin and muscle so that the free ends of the pins may be secured in holes drilled in the bone parts. The pins of one holder are adapted for entering the bone distal the wrist and the pins of the other holder are adapted for entering the bone proximal the wrist. The pin adapted for entering the bone distal the fracture is operatively connected to a compound arc gear adapted to move the wrist through a predetermined path of flexion or extension. The compound arc gear has a plurality of sections each of predetermined varying radius of curvatures to correspond to the physiologic path of flexion or extension of the patient fitted with the device.

23 Claims, 7 Drawing Sheets

ARCUATE FIXATOR

BACKGROUND OF THE INVENTION

The invention relates to the field of fixators which are used to hold bone parts in a fixed position. Specifically, the present invention is used to hold a hand in a fixed position with respect to the wrist bone and the arm bone when there has been a fracture of the wrist or other wrist disorders.

The fixator is a device which is fixed to the forearm and to the hand by a series of threaded pins inserted into the forearm and hand bones. When such a device is used, there is usually no necessity for a cast. The problem with using existing fixators is that the hand cannot be moved until bone healing takes place. Because the hand is held in a rigid position for a long duration, an extreme stiffness develops in the joint after the fracture has healed. Devices have been developed which permit some movement of the hand under controlled circumstances and prevent this stiffness from developing. These devices, however, have had a very limited range of flexing of the hand with respect to the wrist. Such devices include ball joints which are used on the bar which connects the two sets of pins, and as a result thereof, have a limited range of flexibility.

In an attempt to permit greater movement of the hand with respect to the wrist, various arcuate gears have been developed. Particularly, U.S. Pat. Nos. 2,250,417 to Ettinger, 4,185,623 to Volkov et al., and 4,488,542 to Helland disclose apparatus for setting of bone parts including arcuate gears or guides connecting articulated parts such that the fixator may be shifted along its own axis to provide movement to the limb. The disadvantage with these apparatus is that they do not correspond to the physiologic path of flexion or extension of the patient fitted with the device.

With the above problems in mind, it is desirable to provide a fixator used to hold a wrist in a fixed position with respect to the wrist bone and forearm bones when there has been a fracture of the wrist or other wrist disorder yet allowing some movement of the wrist under controlled circumstances and preventing stiffness in the joint from developing.

It is further been found desirable to provide a fixator used to hold a wrist in a fixed position which includes a compound curve gear adapted to move the wrist through a predetermined path of flexion or extension.

It has further been found desirable to provide a fixator used to hold a wrist in a fixed position which includes a compound curve gear having a plurality of sections each of predetermined varying radius of curvatures which correspond to the physiologic path of flexion or extension of the patient fitted with the device.

The present invention is directed towards solving these problems and provides a workable and economic solution to them.

SUMMARY OF THE INVENTION

The present invention relates to a device for use in setting of bone parts of a patient at the site of the fracture or other wrist disorders. Specifically, this device includes a rigid member adjustable in length by an adjustable wheel. A pair of holders are fastened to the rigid member and each carry at least one transcutaneous pin which is intended to penetrate the skin and muscle so that the free end of the pins may be secured in holes drilled in the bone parts. The pins of one holder are adapted for entering the bone distal the wrist, namely the metacarpals, and the pin of the other holder adapted for entering the bone proximal the fracture, namely the radius.

In accordance with one of the general objects of the present invention, the wrist may be moved through a predetermined path of flexion or extension as a result of the metacarpals being operatively connected to a compound arc gear. The compound arc gear has a plurality of sections each of predetermined varying radius of curvatures to correspond to the physiologic path of flexion or extension of the patient fitted with the device.

Furthermore, the compound arc gear of the present invention includes an arcuate rack which is disposed adjacent to the front surface of the rack between upper and lower stops. The arcuate rack is in meshing engagement with a toothed gear which is rotatably coupled to a control member such that when the control member is rotated, the wrist may be either flexed or extended. Upon actuation of the control member, the toothed gear will travel a corresponding predetermined distance along the compound arc gear.

Other objects and advantages of the invention will become apparent from the following detailed description and from the appended drawings in which like numbers have been used to describe like parts of the several views.

BRIEF DESCRIPTION OF THE DRAWINGS OF THE PREFERRED EMBODIMENT

DESCRIPTION OF THE PREFERRED EMBODIMENT

Figure 1:
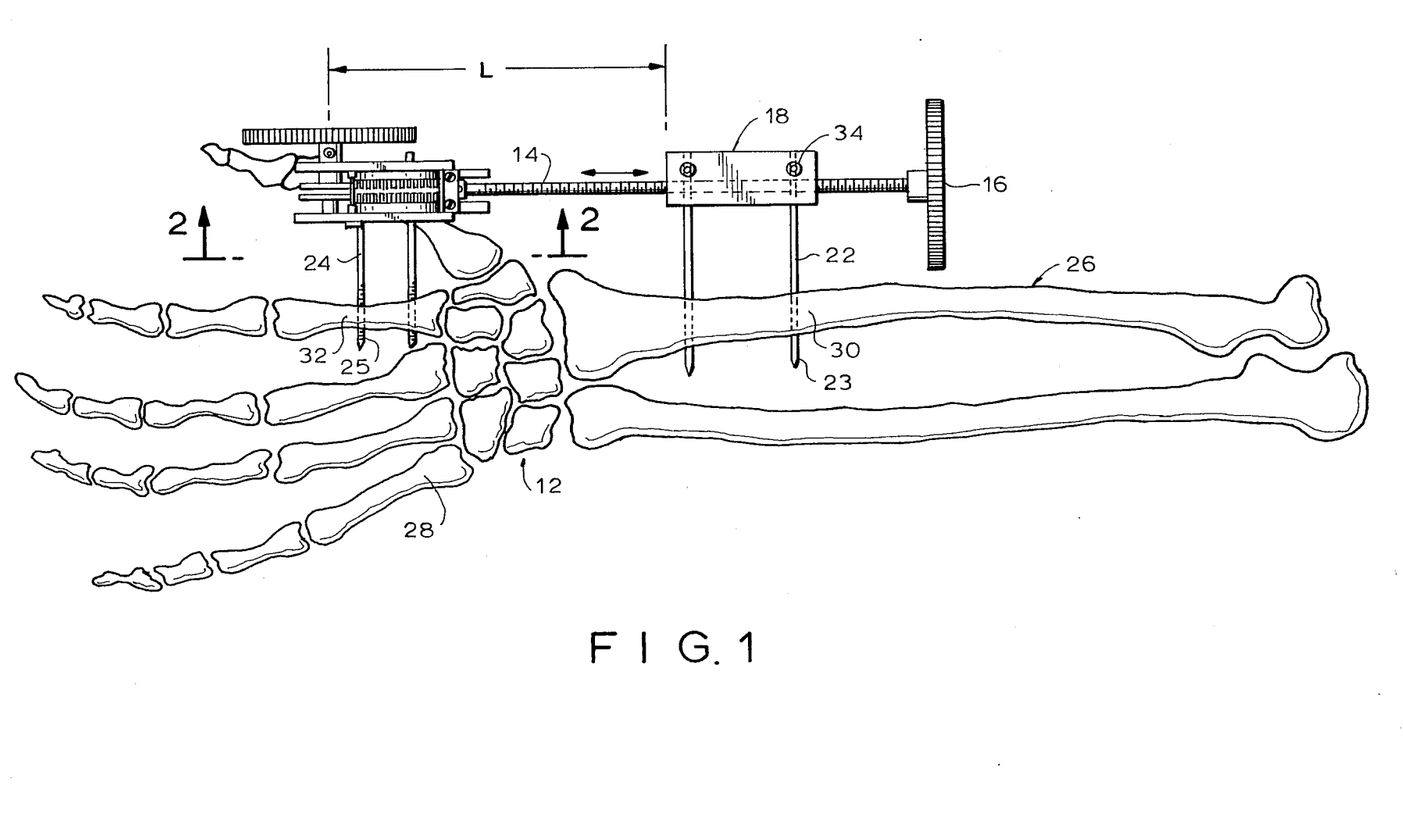
FIG. 1 is a top elevational view of the present invention positioning the bone parts distal and proximal to the wrist in generally the same horizontal plane.

Referring now to FIG. 1, a device 10 for use in setting of fractures of the distal radius or carpal bones at 12 or other conditions of the wrist, is illustrated. The present invention includes a generally horizontal rigid rod member 14 which is adjustable along its length by turning an adjustable wheel 16 for different hand or limb sizes.

In order to secure rigid rod member 14 adjacent to the limb, a pair of holders 18 and 20 are fastened to member 14 with each arm carrying transcutaneous pins 22 and 24, respectively. The free ends 23 and 25 of pins 22 and 24 are secured in holes, such as 30 and 32, which are drilled into the bone parts. Pins 22 of holder 18 are adapted for entering the bone below or proximal to the fracture (in the case of the wrist, the radius 26). Pins 24 of the other holder 20 are adapted for entering the bone distal or above the fracture (in the case of the wrist, the metacarpals 28). Pins 22 and 24 are mounted to the holders 18 and 20 by conventional fasteners 34 and 36, such as a rivet, screw, or the like.

In accordance with one of the objects of the present invention, the bone distal the wrist (the metacarpal 28) is adapted to move through a predetermined path of flexion or extension as a result of the pins 24 adapted for entering the metacarpal 28 being operatively connected to a compound arc gear 40. As will be discussed below, compound arc gear 40 can be patterned to match the physiologic path of flexion and extension or altered to suit the particular needs of the patient or clinical situation. Compound arc gear 40 is mounted to the holder 20 by means of a fastener 42, such as a screw, rivet or the like.

The compound arc gear 40 is situated between a supporting bracket 44 which is adjustable along the length of the rigid rod member 14 by a collar 48 being fixedly retained adjacent to member 14 by a set screw 46. The supporting bracket 44 is retained generally within the horizontal plane of the rod member 14 as a result of a knob 47 at one end of the rod member 14 being engaged within a recess 49 of supporting bracket 44. Supporting bracket 44 also has upper and lower rod member 45a and 45b extending through the supporting member generally perpendicular to the longitudinal axis of the supporting member.

The compound arc gear describes separate flexion and extension arcs and is adapted to move the metacarpals 28 distal the fracture through a predetermined path of flexion or extension. In order to accomplish these results, compound arc gear 40 includes an arcuate rack 50 positioned between support columns 51a and 51b of the compound gear assembly. The arcuate rack 50 includes a plurality of spaced-apart teeth 52 extending along the front edge 53 of compound arc gear 40. The teeth 52 extend along the front edge 53 of gear 40 between upper and lower stops 60 and 62, respectively. The vertical distance along the gear 40 between stops 60 and 62 defines the limit of vertical movement during the flexion and extension arcs of the bone parts distal the fracture.

The movement of the bone distal the wrist results from the cooperation between a toothed gear 54 and arcuate rack teeth 52. Arcuate rack teeth 52 are in meshing engagement with the toothed dual gear 54 nd its side teeth members 54a and 54b. The toothed gear 54 is rotatably coupled to a control member 56 by a shaft 58 such that the toothed gear rides along the rack between upper and lower stops 60 and 62 upon rotation of control member 56, such as by manually turning the control member. As a result of the control member, the toothed gear 54 will travel a corresponding predetermined distance along the compound arc gear 40. Similarly, the control member 56 could be replaced by a motor (not shown) to drive the toothed gear 54 along the arcuate rack 50.

Figure 2:
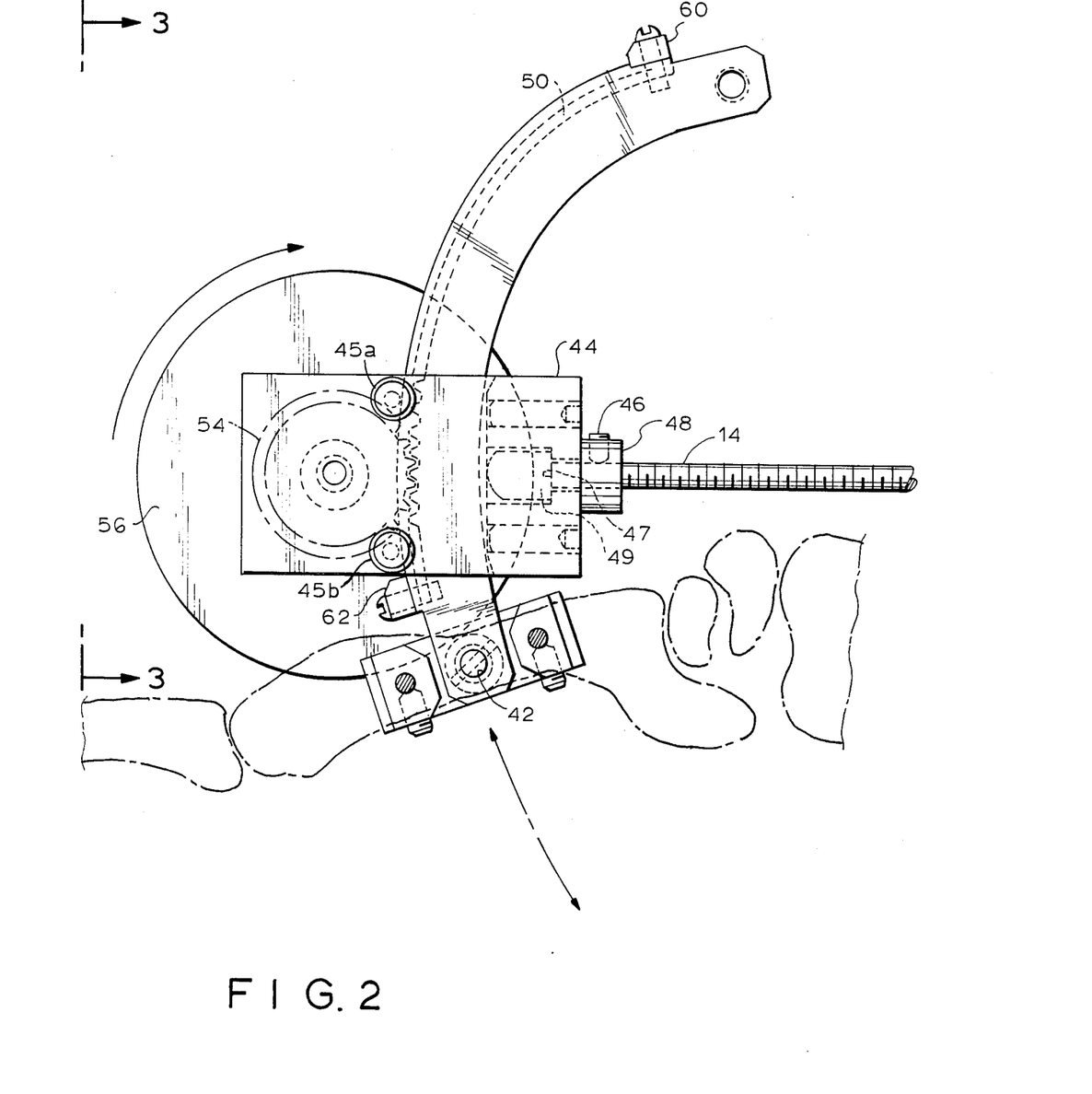
FIG. 2 is a side view taken along line 2—2 of FIG. 1.
Figure 3:
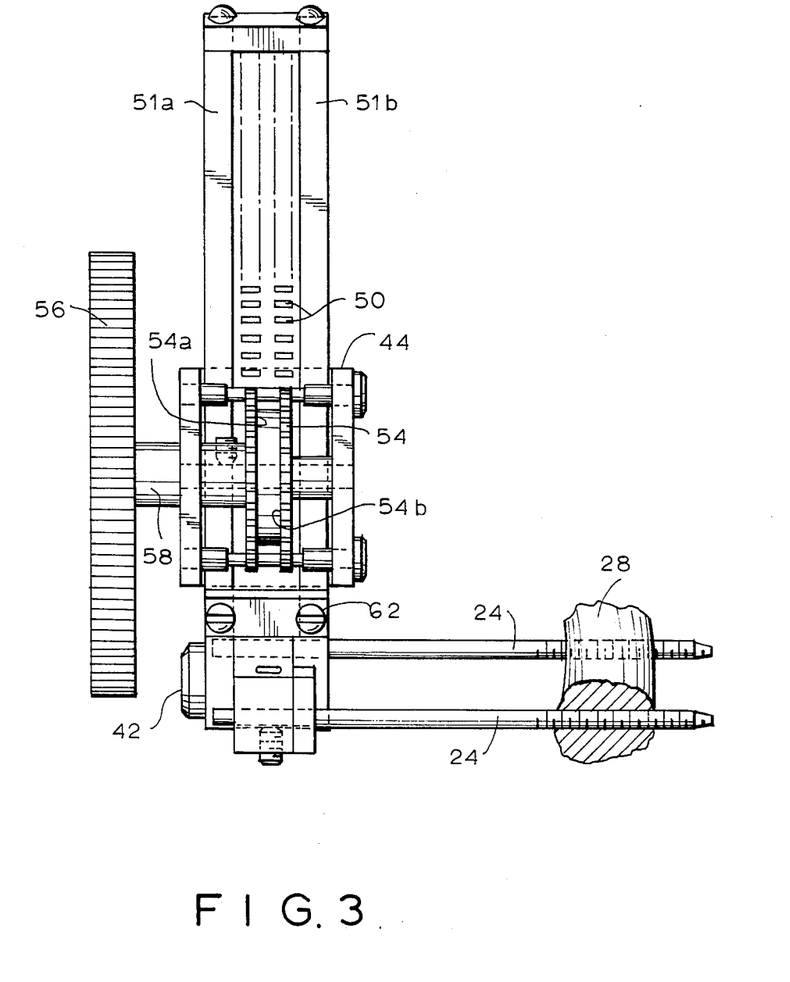
FIG. 3 is a front view of the present invention taken along line 3—3 of FIG. 2.
Figure 4:
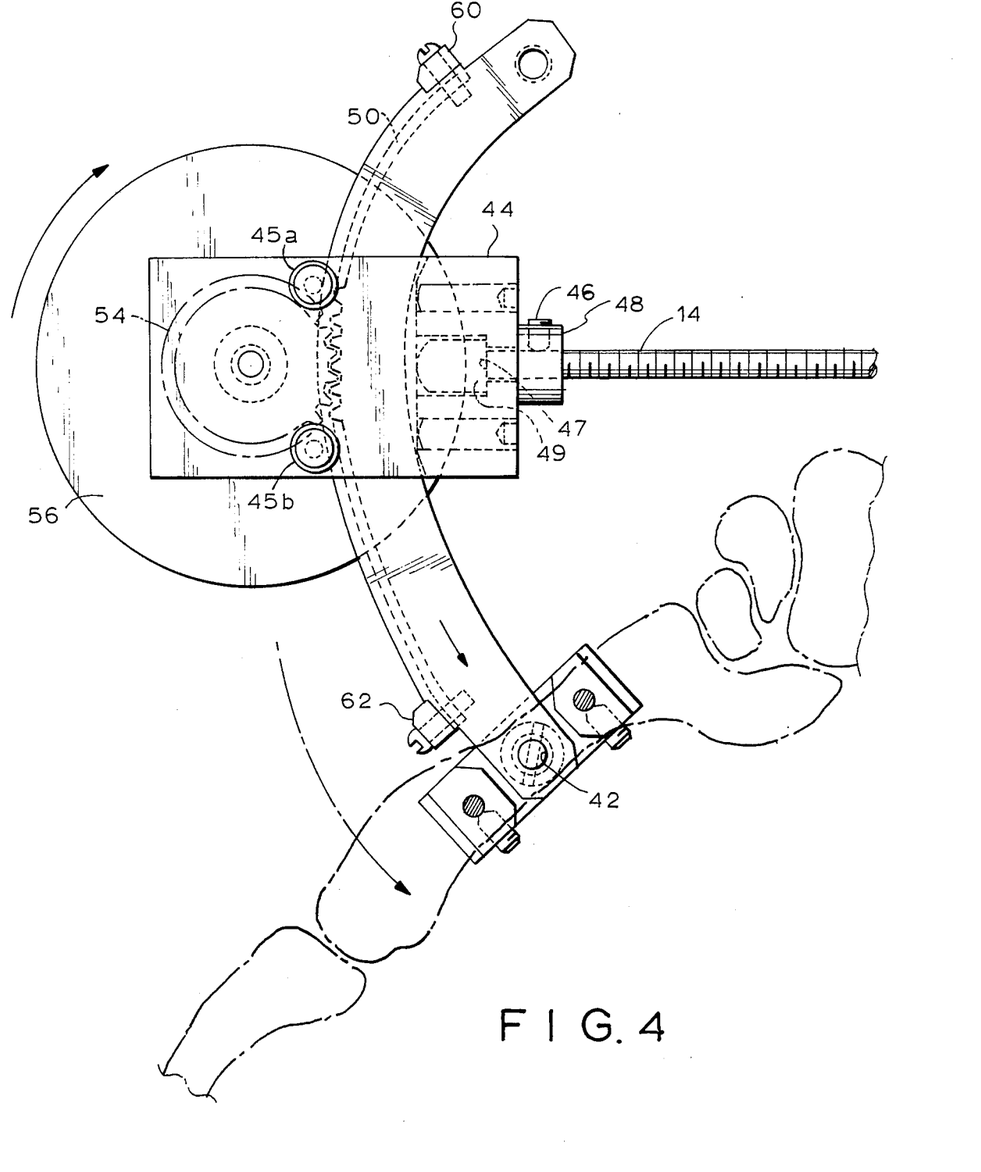
FIG. 4 is a side elevational view of the present invention illustrating the flexion arc.
Figure 5:
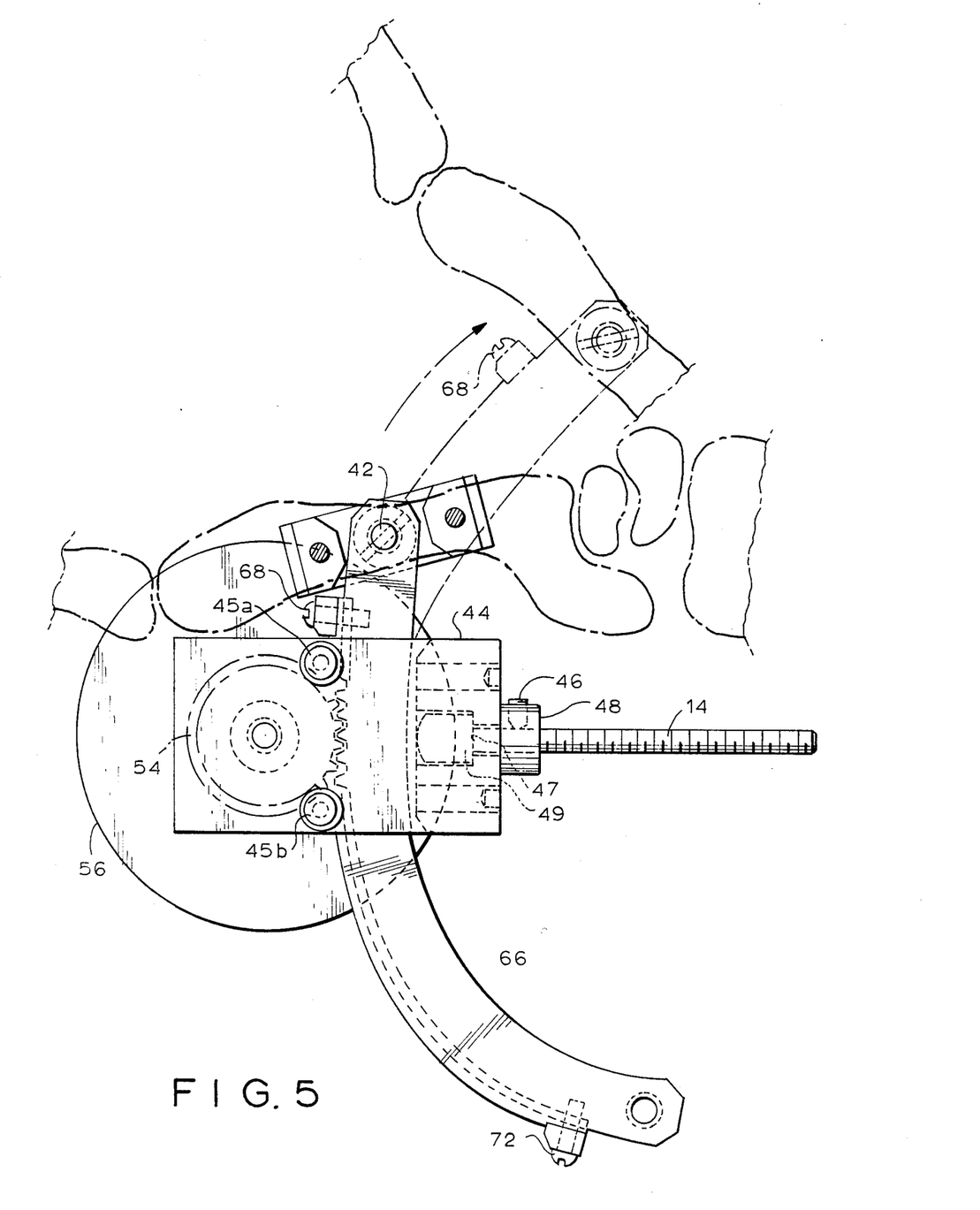
FIG. 5 is a side elevational view of the present invention illustrating the extension arc.

The movement of the bone distal to the wrist through a predetermined path of flexion or extension is specifically illustrated in FIG. 2 (the hand in a generally horizontal or rest position), FIG. 4 (the flexion arc), and FIG. 5 (the extension arc). Specifically referring to FIG. 2, the initial position of the flexion arc, the right-hand is in a generally horizontal position with respect to the arm. The wheel 16 is turned so that the distance L along the member 14 between holders 18 and 20 may be varied to fit the individual patent's hand. Supporting member 44 is positioned along the member 14 at the desired predetermined location by collar 48 being retained adjacent member 14 by set screw 46. The supporting member is also fixed along the longitudinal axis of member 14 by knob 47 of member 14 being supported within recess 49.

The flexion compound are gear 40 is removably insertable between supporting member 44 adjacent toothed gear 54 and fastened to holder 20 by fasteners 42. The flexion compound arc gear 40 extends generally slopingly upwardly from the plane of the arm. Pins 24 of holder 20 are inserted within and secured by the metacarpals 28. Pins 23 of holder 18 are positioned within and secured by the radius 26. In this initial position, the dual toothed gear 54 is positioned in meshing engagement with the arcuate rack teeth 52 adjacent to lower stop 62 of compound arc gear 40.

Upon clockwise rotation of the control member 56, the gear 54 will descend downwardly along rack 50 thereby lowering or flexing the hand with respect to member 14 during th flexion arc, as is shown in FIG. 4. The hand may be lowered by turning control member 56 until the top rod member 45a of the supporting member contacts upper stop 60. The hand can then be returned to its generally horizontal position with respect to the arm as shown in FIG. 2 by turning control member 56 counterclockwise and thereby moving upwardly compound arc gear 40 until the bottom rod member 45b of supporting member 44 contacts lower stop 62.

When the physician desires that the patient's wrist should be moved in an extension arc, a compound arc gear 66 is interchangeably mounted between supporting member 44 adjacent to toothed gear 54 in place of flexion compound arc gear 40. The extension compound arc gear is removably fastened to the holder 20 by fastener 42. Extension compound arc gear 66 extends generally slopingly downwardly from the plane of the arm.

During the extension arc, the toothed gear 54 is initially in meshing engagement with the arcuate rack teeth adjacent to extension compound gear upper stop 68 with the top rod member 45a of supporting member 44 contacting upper stop 68. Upon clockwise rotation of the control member 56, the toothed gear 54 rides along extension compound gear arcuate rack 70 thereby moving the hand angularly upwardly. This upward movement continues until the bottom rod member 45b of supporting member 44 contacts the extension compound gear lower stop 72. The hand can then be returned to its generally horizontal position with respect to the forearm as is illustrated in FIG. 2 by turning control member 56 counterclockwise and thereby moving extension compound arc gear 66 downwardly until upper stop 68 contacts top surface 63 of supporting member 44. The cycle may be continued with the hand moving in a flexion arc by interchangeably replacing flexion compound arc gear 40 for extension compound arc gear 66.

Figure 4A:
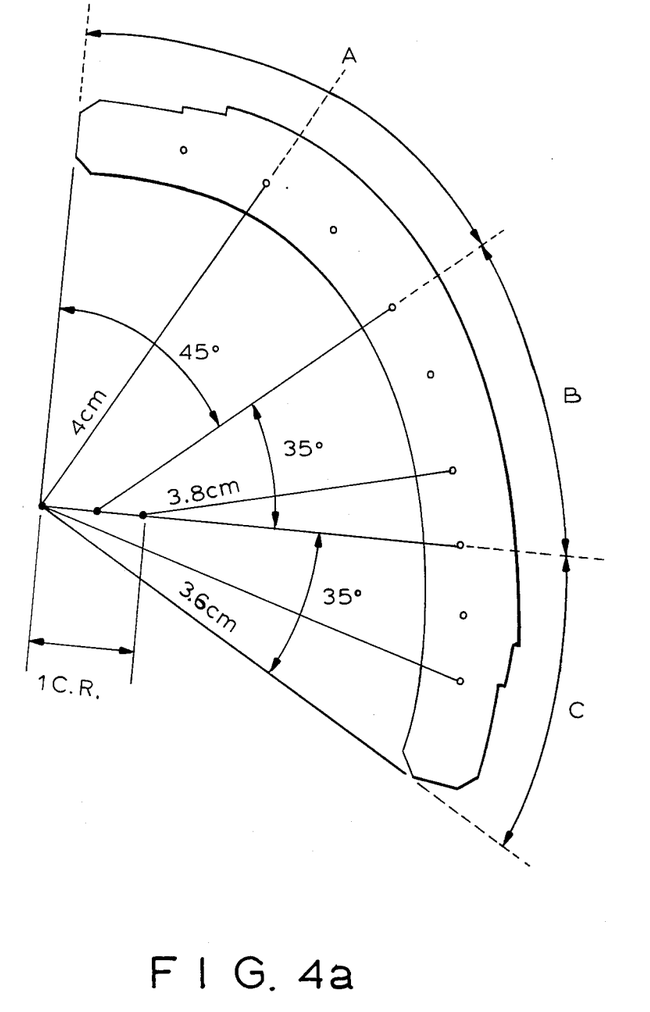
FIG. 4a is a schematic view of the varying radius of curvatures for the dorsal, intermediate and palmar sections of the compound arc gear during the flexion arc.
Figure 5A:
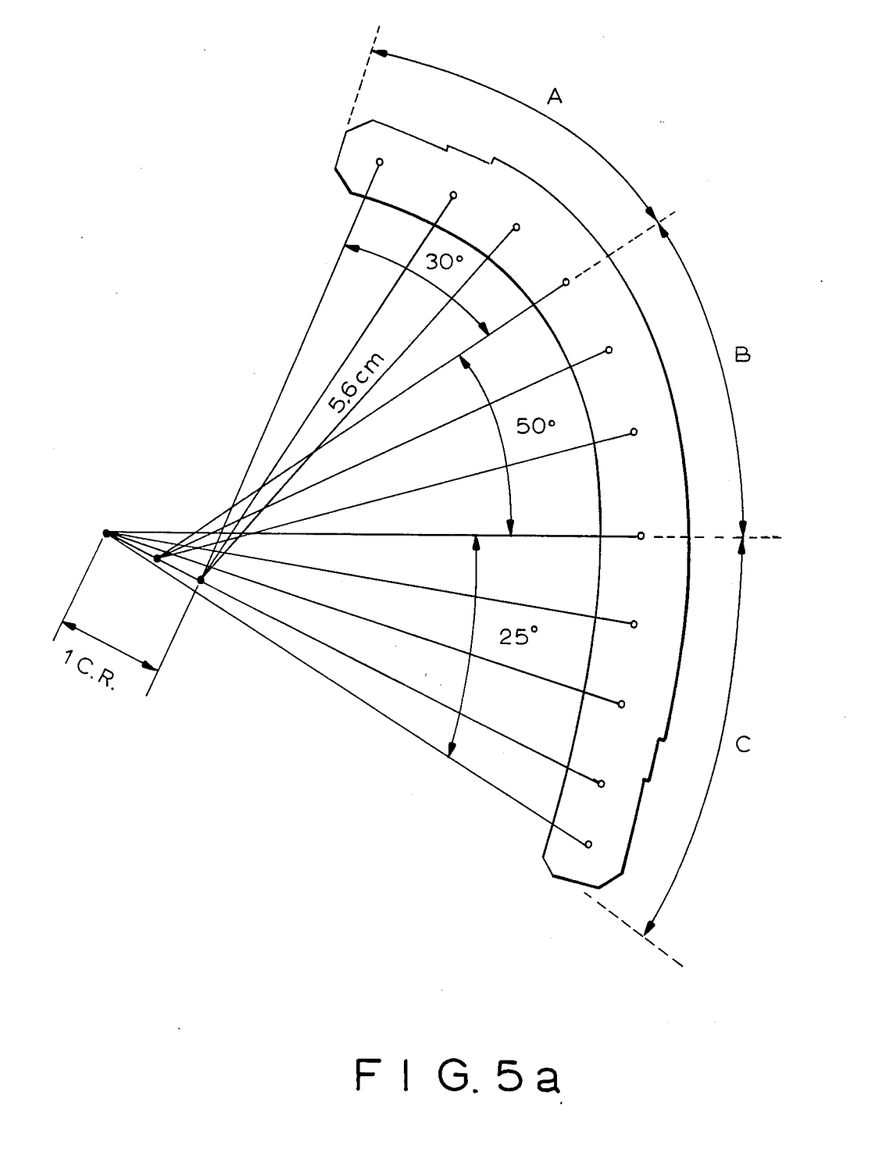
FIG. 5a is a schematic representation of the varying radius of curvatures for the dorsal, intermediate and palmar sections of the compound arc gear during the extension arc.

As shown in FIGS. 4a and 5a, the flexion and extension arcs of the flexion and extension compound arc gears 40 and 66, respectively, have varying radius of curvatures. While these arcs could be subdivided into infinite parts, for the purposes of description it will be divided into three sections, namely the dorsal section, illustrated as section A in FIGS. 4a and 5a which refers to the back or dorsal of the wrist; the middle or intermediate section which is shown as section B in FIGS. 4a and 5a; and the palmar section illustrated as section C in FIGS. 4a and 5a which refers to the palmar aspect of the wrist.

As shown in FIG. 4a in the preferred embodiment, the dorsal section during the flexion arc has a radius of curvature of approximately 4.0 cm for approximately 45° dorsally. The intermediate section has a radius of curvature during the flexion arc of approximately 3.8 cm for approximately 35°. Finally, the palmar section has a radius of curvature during the flexion arc of approximately 3.6 cm for approximately 35°.

Similarly, as best illustrated in FIG. 5a, in the preferred embodiment the dorsal section A has a radius of curvature during the extension arc of approximately 5.6 cm for approximately 30° dorsally. In the intermediate section during the extension arc, the radius of curvature is approximately 6.0 cm for approximately 50°. Finally, in the palmer section, the compound arc gear 40 has a radius of curvature during the extension arc of approximately 6.5 cm for approximately 25°. Thus it can be seen that the flexion and extension compound arc gears 40 and 66 disclosed herein can be patterned to match the physiologic path of flexion or extension and altered to suit the particular needs of a patient or clinical situation. The varying radius of the individual sections of the compound arc gears allow the device to describe separate arcs for flexion and extension.

While the preferred embodiment of the present invention has been described, it should be understood that various changes, adaptations and modifications may be made therein without parting from the spirit of the invention and the scope of the appended claims.

I claim:

1. A device for use in setting of fractured joints or other joint disorders along a limb, comprising a rigid member adjustable in length, a pair of holders fastened to the member and each carrying at least one transcutaneous pin which is intended to penetrate the skin and muscle so that the free ends of the at least one pin may be secured in holes drilled in the bone parts, the at least one pin of one holder adapted for entering the bone distal the joint and at least one pin of the other holder adapted for entering proximal the joint, said pin adapted for entering the bone distal the joint being operatively connected to a compound arc gear means, said compound arc gear means being positioned substantially perpendicular to the longitudinal axis of the limb permitting the bone distal the joint to move in a predetermined generally vertical path of flexion or extension, said compound arc gear means having a plurality of sections each of predetermined varying radius of curvatures to correspond to the physiologic path of flexion or extension of the patient fitted with the device.

2. The device for setting of bone parts at the site of a fracture or other wrist disorders as set out in claim 1 wherein one of the sections of the arc means is a dorsal section having a radius of curvature during the flexion arc of approximately 4.0 cm for approximately 45° dorsally.

3. The device for setting of bone parts at the site of a fracture or other wrist disorders as defined in claim 1 wherein one of the sections of the arc means is a dorsal section having a radius of curvature during the extension arc of approximately 5.6 cm for approximately 30° dorsally.

4. The device for setting of bone parts at the site of a fracture or other wrist disorders as defined in claim 1 wherein one of the sections of the arc means is an intermediate section having a radius of curvature during the flexion arc of approximately 3.8 cm for approximately 35°.

5. The device for setting of bone parts at the site of a fracture or other wrist disorders as defined in claim 1 wherein one of the sections of the arc means is an intermediate section having a radius of curvature during the extension arc of approximately 6.0 cm for approximately 50°.

6. The device for setting of bone parts at the site of a fracture or other wrist disorders as defined in claim 1 wherein one of the sections of the arc means is a palmar section having a radius of curvature during the flexion arc of approximately 3.6 cm for approximately 35°.

7. The device for setting of bone parts at the site of a fracture or other wrist disorders as defined in claim 1 wherein one of the sections of the arc means is a palmar section having a radius of curvature during the extension arc of approximately 6.5 cm for approximately 25°.

8. The device for setting of bone parts at the site of a fracture or other wrist disorders as defined in claim 1 wherein said compound arc gear means is operatively connected to a control means which controls the movement of the bone above the fracture.

9. The device for setting of bone parts at the site of a fracture or other wrist disorders as defined in claim 8 wherein:
said compound arc gear means includes an arcuate rack; and
said control means is in rotational engagement with a toothed gear wherein said toothed gear is in meshing engagement with the arcuate rack so that upon actuation of the control means, the toothed gear will travel a corresponding predetermined distance along the compound arc gear means.

10. The device for setting of bone parts at the site of a fracture or other wrist disorders as defined in claim 1 wherein said control means and said compound arc gear means are operatively connected to said rigid member by a supporting bracket.

11. The device for setting of bone parts at the site of a fracture or other wrist disorders as defined in claim 10 wherein said supporting bracket is adjustable along the rigid member by screw means so that the control means and the compound arc gear means are adjustable along the length of the rigid member to correspond to the placement of the transcutaneous pins entering the bone distal the wrist for each individual patient.

12. The device for setting of bone parts at the site of a fracture or other wrist disorders as defined in claim 1 wherein the distance between the center of rotation of the control means and the holder carrying the transcutaneous pins capable of entering proximal the wrist is variable by means of an adjustable wheel fitted to one end of the rigid member.

13. The device for setting of bone parts at the site of a fracture or other wrist disorders as defined in claim 1 wherein said compound arc gear means is a flexion compound arc gear.

14. The device for setting of bone parts at the site of a fracture or other wrist disorders as defined in claim 1 wherein said compound arc gear means is an extension compound arc gear.

15. The device for setting of bone parts at the site of the fracture or other wrist disorders as defined in claim 1 wherein the compound arc gear means includes a flexion and extension compound arc gear interchangeably mountable to the holder adapted for entering the bone distal the wrist.

16. A device for use in setting of bone parts for a fractured wrist or other wrist disorders along a limb of a patient comprising a rigid member adjustable in length, a pair of holders fastened to the members and each carrying at least one transcutaneous pin which is intended to penetrate the skin and muscle so that the free end of the at least one pin may be secured in holes drilled in the bone parts, the at least one pin of one holder adapted for entering the bone distal the fracture and the at least one pin of the other holder adapted for entering proximal the fracture, the at least one pin adapted for entering the bone distal the wrist being operatively connected to a compound arc gear means which is positioned substantially perpendicular to the longitudinal axis of the limb and permits the bone distal the wrist to move in a predetermined generally vertical path of flexion or extension, said compound arc gear means having a plurality of sections each of predetermined varying radius of curvatures to correspond to the physiologic path of flexion or extension of the patient fitted with the device.

17. The device for setting of bone parts for a fractured wrist or other wrist disorders as defined in claim 16 wherein one of the sections of the arc means is a dorsal section having a radius of curvature during the flexion arc of approximately 4.0 cm for approximately 45° dorsally.

18. The device for setting of bone parts for a fractured wrist or other wrist disorders as defined in claim 16 wherein one of the sections of the arc means is a dorsal section having a radius of curvature during the extension arc of approximately 5.6 cm for approximately 30° dorsally.

19. The device for setting of bone parts for a fractured wrist or other wrist disorders as defined in claim 16 wherein one of the sections of the arc means is an intermediate section having a radius of curvature during the flexion arc of approximately 3.8 cm for approximately 35°.

20. The device for setting of bone parts for a fractured wrist or other wrist disorders as defined in claim 16 wherein one of the sections of the arc means is an intermediate section having a radius of curvature during the extension arc of approximately 6.0 cm for approximately 50°.

21. The device for setting of bone parts for a fractured wrist or other wrist disorders as defined in claim 16 wherein one of the sections of the arc means is a palmar section having a radius of curvature during the flexion arc of approximately 3.6 cm for approximately 35°.

22. The device for setting of bone parts for a fractured wrist or other wrist disorders as defined in claim 16 wherein one of the sections of the arc means is a palmar section having a radius of curvature during the flexion arc of approximately 6.5 cm for approximately 25°.

23. A device for use in setting of fractured joints or other joint disorders along a limb, comprising a rigid member adjustable in length, a pair of holders fastened to the member and each carrying at least one transcutaneous pin which is intended to penetrate the skin and muscle so that the free ends of the at least one pin may be secured in holes drilled in the bone parts, the at least one pin of one holder adapted for entering the bone distal the joint and the at least one pin of the other holder adapted for entering proximal the joint, said pin adapted for entering the bone distal the joint being operatively connected to a compound arc gear means which is positioned substantially perpendicular to the longitudinal axis of the limb and permits the bone distal the joint to move in a predetermined generally vertical path of flexion or extension.

* * * * *